(12) United States Patent
Farooq et al.

(10) Patent No.: US 6,703,112 B1
(45) Date of Patent: *Mar. 9, 2004

(54) ORGANOMETALLIC SALTS FOR INKJET RECEPTOR MEDIA

(75) Inventors: Omar Farooq, Woodbury, MN (US); Clinton P. Waller, Jr., White Bear Lake, MN (US)

(73) Assignee: 3M Innovative Properties Company, St. Paul, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/099,983

(22) Filed: Jun. 19, 1998

(51) Int. Cl.$^7$ ................................................ B41M 5/00
(52) U.S. Cl. ............................... 428/195.1; 428/305.5; 427/261; 347/105
(58) Field of Search .................... 428/195, 207, 428/305.5, 306.6, 308.4, 308.8, 411.1, 913, 195.1; 427/258, 261; 347/96, 105; 562/30, 45, 88, 405, 432, 480

(56) References Cited

U.S. PATENT DOCUMENTS

| | | |
|---|---|---|
| 4,247,498 A | 1/1981 | Castro .......................... 264/41 |
| 4,419,388 A | 12/1983 | Sugiyama et al. .......... 427/288 |
| 4,474,847 A | 10/1984 | Schröder et al. ............. 428/323 |
| 4,539,256 A | 9/1985 | Shipman ................... 428/315.5 |
| 4,547,405 A | 10/1985 | Bedell et al. ................ 427/256 |
| 4,554,181 A * | 11/1985 | Cousin et al. ............... 427/261 |
| 4,613,441 A | 9/1986 | Kohno et al. .......... 210/500.36 |
| 4,649,064 A * | 3/1987 | Jones .......................... 427/256 |
| 4,726,989 A | 2/1988 | Mrozinski ................ 428/315.5 |
| 4,732,786 A | 3/1988 | Patterson et al. ........... 427/261 |
| 4,741,969 A | 5/1988 | Hayama et al. .............. 428/514 |
| 4,775,594 A | 10/1988 | Desjarlais ................... 428/421 |
| 4,781,985 A | 11/1988 | Desjarlais ................... 428/421 |
| 4,867,881 A | 9/1989 | Kinzer ........................ 210/490 |
| 4,877,680 A | 10/1989 | Sakaki et al. ............... 428/332 |
| 4,892,779 A | 1/1990 | Leatherman et al. ........ 428/220 |
| 4,903,039 A | 2/1990 | Light .......................... 346/1.1 |
| 4,903,040 A | 2/1990 | Light .......................... 346/1.1 |
| 4,935,307 A | 6/1990 | Iqbal et al. .................. 428/500 |
| 4,954,395 A | 9/1990 | Hasegawa et al. ........ 428/318.4 |
| 5,079,319 A | 1/1992 | Mueller ................. 526/238.23 |
| 5,084,340 A | 1/1992 | Light .......................... 428/327 |
| 5,102,731 A | 4/1992 | Takimoto et al. ........... 428/323 |
| 5,120,594 A | 6/1992 | Mrozinski ................... 428/195 |
| 5,126,194 A | 6/1992 | Light .......................... 428/327 |
| 5,126,195 A | 6/1992 | Light .......................... 428/327 |
| 5,141,790 A | 8/1992 | Calhoun et al. .............. 428/40 |
| 5,147,410 A | 9/1992 | Heindl et al. .................. 8/555 |
| 5,156,674 A * | 10/1992 | Cells ........................... 106/20 |
| 5,206,071 A | 4/1993 | Atherton et al. ............. 428/195 |
| 5,208,092 A | 5/1993 | Iqbal ........................... 428/195 |
| 5,220,346 A * | 6/1993 | Carreira et al. .............. 346/1.1 |
| 5,229,207 A | 7/1993 | Paquette et al. ............. 428/355 |
| 5,262,238 A | 11/1993 | Trouve et al. ............... 428/402 |
| 5,296,277 A | 3/1994 | Wilson et al. ................. 428/40 |
| 5,302,437 A | 4/1994 | Idei et al. .................... 428/195 |
| 5,342,688 A | 8/1994 | Kitchin et al. .............. 428/402 |
| 5,362,516 A | 11/1994 | Wilson et al. ........... 427/207.1 |
| 5,374,475 A | 12/1994 | Wälchli .................... 428/304.4 |
| 5,380,044 A | 1/1995 | Aitkens et al. ................ 283/67 |
| 5,389,723 A | 2/1995 | Iqbal et al. .................... 525/57 |
| 5,428,383 A * | 6/1995 | Shields et al. ................. 347/96 |
| 5,429,860 A | 7/1995 | Held et al. ................... 428/195 |
| 5,443,727 A | 8/1995 | Gagnon ...................... 210/490 |
| 5,445,868 A * | 8/1995 | Harasawa et al. ........... 428/206 |
| 5,500,668 A * | 3/1996 | Malhotra et al. ............ 347/105 |
| 5,518,534 A * | 5/1996 | Pearlstine et al. ......... 106/20 R |
| 5,537,137 A | 7/1996 | Held et al. ................... 347/105 |
| 5,569,529 A | 10/1996 | Becker et al. ............... 428/331 |
| 5,605,750 A | 2/1997 | Romano et al. .......... 428/304.4 |
| 5,624,484 A | 4/1997 | Takahashi et al. ........ 106/31.75 |
| 5,640,187 A | 6/1997 | Kashiwazaki et al. ....... 347/101 |
| 5,677,067 A * | 10/1997 | Kojima et al. ............ 428/478.2 |
| 5,679,143 A | 10/1997 | Looman .................... 106/20 R |
| 5,681,660 A | 10/1997 | Bull et al. ................... 428/500 |
| 5,683,793 A | 11/1997 | Malhotra et al. ............ 428/216 |
| 5,686,602 A | 11/1997 | Farooq et al. ............... 536/101 |
| 5,688,603 A | 11/1997 | Iqbal et al. .................. 428/532 |
| 5,695,820 A | 12/1997 | Davis et al. ................. 427/261 |
| 5,707,722 A | 1/1998 | Iqbal et al. ............... 428/304.4 |
| 5,731,430 A | 3/1998 | Fuertes et al. ................ 536/58 |
| 5,747,148 A | 5/1998 | Warner et al. ............... 428/212 |
| 5,789,342 A | 8/1998 | Evans et al. ................. 503/227 |
| 5,800,919 A | 9/1998 | Peacock et al. ............. 428/355 |
| 5,863,662 A | 1/1999 | Hornby et al. .............. 428/483 |
| 5,874,143 A | 2/1999 | Peloquin et al. ............ 428/40.1 |
| 5,885,337 A * | 3/1999 | Nohr et al. ................ 106/31.27 |
| 6,054,213 A | 4/2000 | Peacock et al. ............. 428/355 |
| 6,071,614 A | 6/2000 | Farooq ........................ 428/403 |
| 6,177,187 B1 | 1/2001 | Niemoller et al. .......... 428/327 |

FOREIGN PATENT DOCUMENTS

| | | |
|---|---|---|
| DE | 196 28 341 | 1/1998 |
| EP | 0 199 874 | 11/1986 |
| EP | 0 457 728 A1 | 11/1991 |

(List continued on next page.)

OTHER PUBLICATIONS

Porterfield, William W., *Inorganic Chemistry*, Addison–Wesley Publishing Company, Inc., p. 133, 1984.*

(List continued on next page.)

*Primary Examiner*—Marie Yamnitzky

(57) ABSTRACT

Organometallic salts useful for inkjet receptor media are disclosed. The organometallic salt can be a multivalent metal derivative of an aromatic carboxylic, sulfocarboxylic, sulfophenolic, or combination thereof. The aromatic moiety can be a simple aromatic, a condensed aromatic, a heterocyclic aromatic or a combination thereof. The multivalent metal ion can be derived from the group IIA to VIA and Group IB to VIIIB of elements in the Periodic Table. The organometallic salt simultaneously releases the multivalent metal cation and the organic acid anion for both pigment management and ink-drying.

21 Claims, No Drawings

FOREIGN PATENT DOCUMENTS

| | | |
|---|---|---|
| EP | 0 484 016 A1 | 5/1992 |
| EP | 0 570 515 B1 | 11/1993 |
| EP | 0 614 771 A1 | 9/1994 |
| EP | 0 627 324 A1 | 12/1994 |
| EP | 0 661 168 | 7/1995 |
| EP | 0 667 246 A1 | 8/1995 |
| EP | 0 673 782 A2 | 9/1995 |
| EP | 0 716 931 A1 | 6/1996 |
| EP | 0 736 392 | 10/1996 |
| EP | 0 791 473 A2 | 8/1997 |
| EP | 0 839 880 A1 | 5/1998 |
| EP | 0 876 914 A1 | 11/1998 |
| EP | 0 878 319 A2 | 11/1998 |
| EP | 0 894 641 | 2/1999 |
| EP | 0 897 808 A1 | 2/1999 |
| GB | 2 147 003 | 5/1985 |
| JP | 61-063476 | 1/1986 |
| JP | 61-41585 | 2/1986 |
| JP | 61-261089 | 11/1986 |
| WO | WO 93/01938 | 2/1993 |
| WO | WO 93/25595 | 12/1993 |
| WO | WO 95/28285 | 10/1995 |
| WO | WO 96/18496 | 6/1996 |
| WO | WO 97/20697 | 6/1997 |
| WO | WO97/33758 | 9/1997 |
| WO | WO 98/02314 | 1/1998 |
| WO | WO 98/05504 | 2/1998 |
| WO | WO 98/05512 | 2/1998 |
| WO | WO98/29516 | 7/1998 |
| WO | WO 98/30749 | 7/1998 |
| WO | WO 99/03685 | 1/1999 |
| WO | WO 99/06219 | 2/1999 |
| WO | WO 99/07588 | 2/1999 |

OTHER PUBLICATIONS

R.E. Kesting, *Synthetic Polymeric Membranes*: Structural Perspective, 2d ed., John Wiley & Sons, 1985 Chapter 7, pp. 237–285. (no month).

Hornby et al., "Acrylidone Anionic Copolymers," International Specialty Products (brochure), Reprinted from *Soap/Cosmetics/Chemical Specialties* (Jun. 1993) 5 pgs.

International Specialty Products (brochure), Industrial Reference Guide "Polymers—Polyvinylpryrrolidone," 2 pgs. (date not given).

International Specialty Products (brochure), Polyvinylpyrrolidone Polymers, "PVP", 16 pgs (date not given).

International Specialty Products (brochure), "Acrylidone™ Anionic Polymers," 6 pgs. (date not given).

*Encyclopedia of Polymer Science and Engineering,* vol. 17, pp. 204–214, 229, 234–235, John Wiley and Sons, Inc. (1989). (no month).

\* cited by examiner

ORGANOMETALLIC SALTS FOR INKJET RECEPTOR MEDIA

FIELD OF INVENTION

This invention relates to the use of organometallic salts for pigment management in microporous inkjet receptor media.

BACKGROUND OF INVENTION

Inkjet imaging techniques have become vastly popular in commercial and consumer applications. The ability to use a personal computer and desktop printer to print a color image on paper or other receptor media has extended from dye-based inks to pigment-based inks. The latter provide brilliant colors and more durable images because pigment particles are contained in a dispersion before being dispensed using a thermal inkjet print head, such as those commercially available from Hewlett Packard Corporation or LexMark Corporation in inkjet printers commercially available from Hewlett Packard Corporation, Encad Inc., Mimaki Corporation, and others.

Ink jet printers have been in general use for wide-format electronic printing for applications such as, engineering and architectural drawings. Because of the simplicity of operation, economy of ink jet printers, and improvements in ink technology the inkjet imaging process holds a superior growth potential promise for the printing industry to produce wide format, image on demand, presentation quality durable graphics.

The components of an ink jet system used for making graphics can be grouped into three major categories:

1 Computer, software, printer.
2 Ink.
3 Receptor sheet.

The computer, software, and printer will control the size, number and placement of the ink droplets and will transport the receptor film. The ink will contain the colorant or pigments which form the image and the receptor film provides the medium which accepts and holds the ink. The quality of the ink jet image is a function of the total system. However, the composition and interaction between the ink and receptor film is most important in an ink jet system.

Image quality is what the viewing public and paying customers will want and demand to see. Many other demands are also placed on the ink jet media/ink system from the print shop, such as rapid drying, humidity insensitivity, extended shelf life, waterfastness and overall handleability. Also, exposure to the environment can place additional demands on the media and ink (depending on the application of the graphic).

Porous membrane is a natural choice to use as an ink jet receptive media because the capillary action of the porous membrane can wick the ink into the pores much faster than the absorption mechanism of film forming water soluble coatings. However, in the past, when a porous coating or film has been employed to achieve desired quick dry, optical density has suffered greatly because the colorant penetrates too deep into the porous network. This type of problem is magnified by printers that dispense high volumes of ink per drop because extra film thickness may be required to hold all the ink. When the pore size and pore volume of the membrane are opened to allow the pigments to penetrate, the pigments can be stratified in the membrane. Meaning, the black, cyan, magenta, and yellow will be predominately found at different depths depending on the order of application. Hence, some of the first color(s) applied is/are optically trapped in the image by subsequent application of other pigmented ink. Furthermore, lateral diffusion of the ink can also be a problem inherent in porous membranes used as receptive media. When pigmented inks are jetted onto a porous film that has a pore size that is too small, color pigments will be filtered on the top of the membrane rendering high image density, but the pigments could easily smear and have the effect of never drying. Also, excess fluid from the ink can coalesce, or even worse, pool and run on the image before the water/glycol carrier is wicked away.

The chemical formulation of the pigmented inkjet ink has considerable complexity due to the requirement of continued dispersion of the pigment particles in the remainder of the ink and during jetting of the ink.

The typical consumer medium for receiving dye-based inkjet inks has been paper or specially coated papers. However, with too much inkjet ink in a given area of the paper, one can see the over-saturation of the paper with the aqueous ink in which dye was dissolved.

As inkjet inks have become more commercially oriented and pigmented-based inks have become more prevalent, different media have been tried in an attempt to control the management of fluids in the ink.

Japanese Patent JP 61-041585 discloses a method for producing printing material using a ratio of PVA/PVP. The disadvantage is inadequate waterfastness and wet rub off properties.

Japanese Patent JP61-261089 discloses a transparent material with cationic conductive resin in addition to a mixture of PVA/PVP. The material is water fast and smudge proof but the wet rub off properties are poor.

European Patent Publication EP 0 716 931 A1 discloses a system using a dye capable of co-ordinate bonding with a metal ion in two or more positions. Again binder resins are used with inorganic pigments in the paper or film. The metal ion was preferred to be jetted on before imaging and additional heating is necessary to complete the reaction. This system was not claiming to be water fast; the focus was long term storage without fading from heat or light.

U.S. Pat. No. 5,537,137 discloses a system to achieve waterfastness by curing with heat or UV light. In the body of the patent, examples of their coatings contained Ca++ from $CaCl_2$. This was added to provide reactive species for the acid groups on the dispersed polymer. The coating remains water soluble until UV or heat curing after imaging.

Hence, the current special ink jet media employ vehicle absorptive components, and sometimes optional additives to bind the inks to the media. As a consequence current media are inherently moisture sensitive and can be fragile to handling and subject to finger smearing. Moreover, the vehicle absorptive components usually consist of water soluble (or swelling) polymers which result in slower printing speeds and dry times.

Pigmented ink delivery systems have also dealt with pigment management systems, wherein the resting location of the pigment particles are managed to provide the best possible image graphic. For example, copending, coassigned, U.S. Pat. No. 5,747,148 (Warner et al.), discloses a pigment management system in which a suitable supporting layer (including in a listing a microporous layer) has a two layer fluid management system: a protective penetrant layer and a receptor layer, both layers containing filler particles to provide two different types of protrusions from the uppermost protective penetrant layer. Electron microphotographs in that application show how the pigment particles of the ink encounter smooth protrusions that provide a suitable topography for pigment particle "nesting" and rocky protrusions that assist in media handling and the like.

Other ink receptors have been disclosed, including U.S. Pat. Nos. 5,342,688 (Kitchin); 5,389,723 and 4,935,307 (both Iqbal et al.); 5,208,092 (Iqbal) 5,302,437 (Idei et al); U.S. Pat. No. 5,206,071 (Atherton et al.); and EPO Patent Publication 0 484 016 A1.

One prior activity has combined a fluid management system with a pigment management system, as disclosed in copending, coassigned, U.S. patent application Ser. No. 08/892,902 now U.S. Pat. No. 6,632,510, the disclosure of which is incorporated herein by reference. The work concerns the use of multivalent metal salts which in aqueous solution releases metal ions and an inorganic anion. Whereas the metal ion plays the role of pigment management system the metal anion does not play any role in the composition except being a cationic partner.

SUMMARY OF INVENTION

In the present work, an organometallic salt improves on the art by rapidly releasing multivalent metal cation which takes care of the pigment management function and an organic anion which provides useful organic acid to control smudgeness and drying of the film. This work, therefore, solves the need for an inkjet receptor to have both a pigment management system for flocculating or agglomerating of incoming ink and a drying agent for the humectants of the ink thus efficiently drying the pigmented inks within a porous substrate.

One aspect of the invention is an inkjet receptor medium, comprising a composition of matter comprised of an organometallic salt of a multivalent metal cation and an organic acid anion.

One aspect of the present invention is to provide a metal salt that releases a metal cation for pigment management and simultaneously releases an organic acid anion of a carboxylic or sulfocarboxylic or phenolic acid or hydroxy or mixed functionalities thereof to take care of the drying aspect of the ink system. "Drying agent" means an agent, component, ingredient or compound which can dry or make the pigment feel dry to touch via chemically or physicochemically occlusion or interaction with certain components such as the humectant or other slow drying components in the pigmented inks used in printing the image onto the receptor medium. Specifically, "dry to touch" means, an indistinguishable "feel" between the imaged and the unimaged areas of the substrate regardless of whether, technically, all volatiles have evaporated from the imaged area.

One feature of the present invention is a multivalent organometallic salt that releases a multivalent metal ion for pigment management and an anion of an organic acid consisting of a carboxylic and/or a sulfonic acid or hydroxyl or a phenolic or a mixed functionality thereof in a composition in an aqueous solution wherein the acid works as an ink-drying agent in a film coated with the said composition.

One advantage of the present invention is that both the multivalent metal cation and the organic acid can be derived from the same salt/component. This advantage avoids the necessity of providing two different components to a porous substrate. Furthermore, the procedure minimizes the possibility that the coating solutions become contaminated with any undesirable residue or components or by product-compounds as contaminants.

Another feature of the present invention is that a composition including the organometallic salt, surfactant and the migration inhibitor uses a lesser amount of total solids to achieve comparable performance. Thus, one can minimize concentration to obtain equivalent performance or maximize concentration to achieve previously-unattainable performance.

Other features and advantages of the invention will be disclosed in relation to the embodiments of the invention.

EMBODIMENTS OF INVENTION

Inkjet Receptor Medium

The inkjet receptor medium can be any porous membrane or film known to those skilled in the art wherein it is desired to print inkjet inks on at least one major surface thereon. Preferably, the medium comprises an inkjet receptor medium, comprising a porous substrate having a fluid management system and having a pigment management system in contact with surfaces of pores of the substrate therein, such as disclosed in copending, coassigned, U.S. patent application Ser. No.08/892,902 now U.S. Pat. No. 6,632,510, the disclosure of which is incorporated herein. The pigment management system includes a multivalent metal salt coating or functionalized particulates impregnated in pores of the porous substrate such that they are in contact with surfaces of pores of the porous substrate. One embodiment of that medium is an inkjet receptor comprising a microporous membrane impregnated with an multivalent metal salt together with a surfactant or combination of surfactants chosen for the ink and membrane being employed.

Another embodiment is an inkjet receptor comprising a microporous membrane impregnated with a microporous fluorinated silica agglomerate together with a binder and a surfactant or a combination of surfactants for the ink and membrane being employed.

Another embodiment of that medium is an inkjet receptor comprising a microporous membrane impregnated with a microporous fluorinated silica agglomerate together with a binder and a surfactant or combination of surfactants wherein the surfactants are selected from the group of hydrocarbon-based anionic surfactants, silicon-based non-ionic surfactants or fluorocarbon-based non-ionic based surfactants or a combination thereof.

These receptors, when imaged in an inkjet printer, provide very high density and very high quality images which are tack-free and instantaneously dry to touch.

One embodiment of the present invention is an inkjet receptor comprising a microporous membrane impregnated with an organometallic multivalent salt together with a hydrophilic surfactant and an optional migration inhibitor polymer/copolymer chosen from a series of hydrophilic/hydrophobic polymers/copolymers.

Another embodiment of the present invention is an inkjet medium comprising a microporous membrane impregnated with an organometallic multivalent salt wherein the said salts are derived from various aromatic acids consisting of sulfonic, carboxylic, phenolic, hydroxyl and mixed functionalities thereof and wherein the metal ions may be derived from group IIA to VIA and more preferably from group IB to VIIIB in the Periodic Table. Specific examples, include, but are not limited to, Al, Mg, Zn, Fe, Bi, Ga, Sn, Ca, Ti, Zr, Cu, Co etc.

Nonlimiting examples of organometallic salts useful in the present invention include:.

Metal Sulfocarbolates

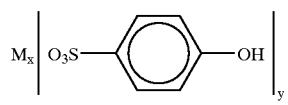

M = Cu, Mg, Co (x:y = 1:2); M = Al, Ga (x:y = 1:3, 2:3)

Metal Hydroquinonesulfonates

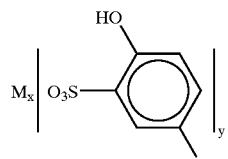

M = Cu, Mg, Co (x:y = 1:2, 2:2); M = Al, Ga, Ti, Zr (x:y = 1:3, 2:3, 2:2)

Metal dihydroxybenzenedisulfonates

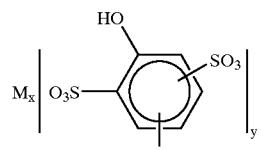

M = Cu, Mg, Co (x:y = 1:1, 1:2); M = Al, Ga, Ti, Zr (x:y = 1:3, 2:2, 4:3)

Metal Sulfosalicylates

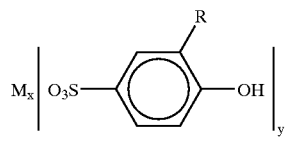

M = Cu, Mg, Co (x:y = 1:2, 1:1); M = Al, Ga, Ti, Zr (x:y = 1:3, 2:3, 3:3)
R = —COOH (Li$^+$, Na$^+$, K$^+$)

Metal Sulfophthalates

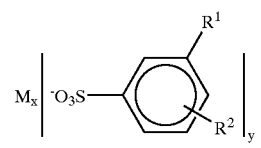

M = Cu, Mg, Co (x:y = 1:1, 2:2. 3:2); M = Al, Ga, Ti, Zr (x:y = 1:3, 2:2, 2:3)
$R_1 = R^2 =$ —COOH (Li$^+$, Na$^+$, K$^+$)

Metal Carboxylates (a)

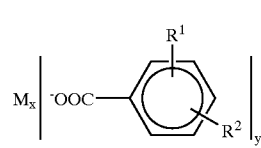

M = Cu, Mg, Co (x:y = 1:1, 2:2. 3:2); M = Al, Ga, Ti, Zr (x:y = 1:3, 2:2, 2:3)
$R^1 =$ —COOH (Li$^+$, Na$^+$, K$^+$), $R^2 =$ —OH

-continued (b)

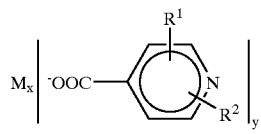

M = Cu, Mg, Co (x:y = 1:1, 2:2. 3:2); M = Al, Ga, Ti, Zr (x:y = 1:3, 2:2, 2:3)
$R^1 =$ —COOH (Li$^+$, Na$^+$, K$^+$), $R^2 =$ —OH

Metal Calix(n) Arene Sulfonates

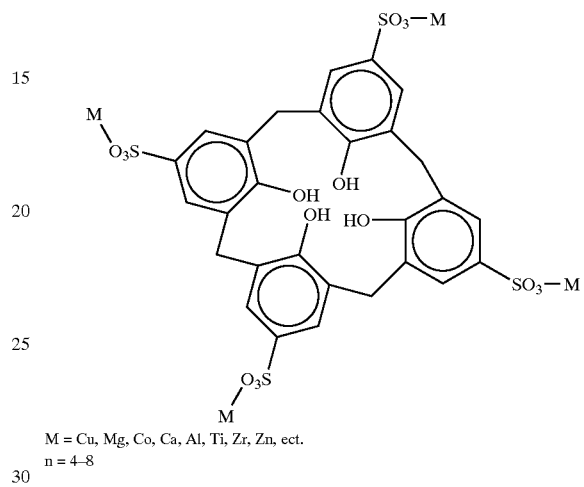

M = Cu, Mg, Co, Ca, Al, Ti, Zr, Zn, ect.
n = 4–8

Another embodiment of the present invention is an inkjet medium comprising a microporous membrane impregnated with an organometallic multivalent salt wherein the salt releases both a multivalent metal cation and an organic acid anion and wherein the metal cation plays the role of pigment management system and the organic acid anion plays the role of a dehydrating or drying agent thus making the image in the membrane smudge-free to touch.

Another embodiment of the present invention is an inkjet medium comprising a microporous membrane impregnated with an organometallic multivalent salt wherein the salt releases both a multivalent metal cation and an organic acid anion—both simultaneously being useful for pigment management system and humectant management system in the ink.

Another embodiment of the present invention is an inkjet coating composition that incorporates an organometallic multivalent salt with a surfactant and a binder only to give a composition which provides 0.33 to 0.25 of the coating weight of that a composition consisting of a metal salt, a surfactant, organic acid and a binder, such as that disclosed in the copending, coassigned U.S. patent application Ser. No 08/892,902 (Waller et al.), now U.S. Pat. No. 6,632,510, which discloses a fluid management system in combination with a pigment management system and which is incorporated by reference as if rewritten herein.

The ink colorant is typically a pigment dispersion having a dispersant that binds to the pigment and that will destabilize, flocculate, agglomerate, or coagulate the pigments on contact with the media component. Depositing each of the colors at or just below the surface of the membrane allowing the carrier fluid to wick into the membrane where the fluid management system can take over while providing a sheltered location for the pigments as managed by the pigment management system.

Porous substrates useful in the present invention include symmetrical membranes, asymmetrical membranes, and porous films also known as skinned membranes. Symmetrical membranes have porosity on opposing major surfaces of approximately the same pore size. Asymmetrical membranes have porosity on opposing major surfaces that are not of similar pore sizes. A skinned membrane has considerable porosity on one major surface but essentially no porosity on the opposing major surfaces.

Nonlimiting examples of commercially available microporous membranes include: nylon and polysulfone membranes from Gelman Sciences, Ann Arbor Mich.; polyolefin membranes from Amoco Corp., Chicago Ill.; and polyolefin, nylon, or ethylene vinyl alcohol membranes from 3M.

A suitable microporous membrane for printing on a 100–140 picoliter per drop size for each color and 300×300 drops per inch printer has a thickness or caliper ranging from about 75 μm to about 200 μm, and preferably from about 100 μm to about 175 μm It is a reality of ink jet printing that as many as four pigment drops, representing each of the four printing colors, are landing on a single spot of the ink jet receptor medium in order to generate any one of the myriad of colors available in ink jet printing.

The microporous membrane can have a porosity value as calculated by measuring the bulk density of the membrane in grams/cm$^3$ from the specific gravity measurement determined according to ASTM-D-792-66 and substituting that value into the following formula:

$$100\times[1\text{-measured density/polymer density}]=\text{porosity},$$

ranging from 20 to about 95 and preferably from about 30 to about 50. Alternatively, the membrane can have a pore volume ranging from about 80 to about 100% of the anticipated ink volume dispensed from a given inkjet printer.

Bubble point is a measurement of the largest effective pore size in a symmetrical membrane that has through-porosity, as measured according to ASTM F-316, and can range from about 0.20 μm to about 2.0 μm and preferably about 0.40 μm to about 0.80 μm.

Surface energy of the porous substrate before treating with the pigment and fluid management systems can range from 20 to 70 dynes/cm as defined in the Third Edition of the POLYMER HANDBOOK by J. Brandrup and E. H. Immergut (1989).

Microporous membranes can be of unlimited length, depending on the size of the roll that can be facilely handled. Usually, commercial quantities of the microporous membrane for feeding into a commercial printer can be a roll having a length in excess of 10 meters, and preferably in excess of 20 meters.

As inkjet media become more useful with wide format inkjet printers, the width of the microporous membrane becomes important from a perspective of imaging productivity and convenient graphic installation. The membrane can have a width ranging from about 0.25 meters to about 2 meters and preferably a width ranging from about 0.60 meters to about 1.2 meters.

More preferably, the inkjet receptor medium uses a Thermally Induced Phase Separated (T.I.P.S.) microporous membrane according the disclosures of U.S. Pat. Nos. 4,539,256 (Shipman et al.), 4,726,989 (Mrozinski), and more particularly 5,120,594 (Mrozinski), and available from 3M. For optimization, the pore size and pore volume of the porous film can be adjusted for the model or make of the ink jet printer to correctly hold the volume of ink dispensed by the printer ensuring the highest possible image quality. The coating on the preferred media/ink set has special utility in the demanding ink jet printing applications found in commercial printing. Thus, one can "fine tune" the properties of these receptors to deal with the variables of inkjet ink delivery, including without limitation: drop volume, porosity of media, and capacity of media to receive ink. Moreover, these media exhibit a complex porosity in its porous material that provides both a tortuous path for fluid management and a tortuous path that ensnares the pigment initially and continually during ink delivery.

Optional Additives

Pigment Drying Agents

Pigment drying agents can be useful in the present invention and can comprise aromatic or aliphatic acids having sulfonic, carboxylic, phenolic or mixed functionalities thereof. Further information can be found in copending, coassigned, U.S. patent application Ser. No. 09/099,961, now U.S. Pat. No. 6,383,612.

Preferably, aromatic sulfonic and carboxylic acids have been found in this invention to be very effective in presence of multivalent metal salts and suitable surfactant and binder, to serve as drying agents for inkjet receptor media. These acids can be of various types, chosen according to properties and distinguished by extent of their solubility in water and how that solubility affects drying performance.

At one end of the range of candidate acids, their higher solubility in water can interfere with other components in the media, such as a migration inhibitor as disclosed in copending, coassigned, U.S. patent application Ser. No. 09/099,956, now U.S. Pat. No. 6,537,650, thereby perhaps requiring a greater concentration of drying agent to be included in the coating. One example of this type of acid is a sulfocarboxylic acid such as sulfosalicylic acid.

At the other end of the range of candidate acids, the candidate acids with lower solubility in water would perform the drying function excellently but could require more aggressive solvent(s) to be impregnated into the media. One example of this type of acid is a phthalic acid so long as it is recognized that impregnating the receptor media will be more challenging because of the acid's lower solubility. To overcome impregnating limitations, lower solubility acid candidates, such as aromatic carboxylic acids, can be derivatized to become a monosodium salt (or any other similar alkali metal salt), the solubility of that salt in water is enhanced. One example of this type of acid-salt is an aromatic carboxylic acid, sodium salt such as ortho-phthalic acid-sodium salt. Furthermore, the aromatic carboxylic acids are also sufficiently soluble in water when the aromatic moiety contains at least one sulfonic acid group attached to the aromatic ring either as acid or as its sodium salt (or other alkali metal salts). Two examples of these candidates are 5-sulfoisophthalic acid and also its monosodium salt.

Other functional groups such as—OH group can be attached to the aromatic moiety to increase the solubility of the aromatic carboxylic group. Examples in this category are hydroxy-aryldicarboxylic acid isomers.

A related factor to choice of lower water solubility candidate acid is the amount of the acid to be included in the receptor media. The relationship is generally such that the lower solubility acid candidates are needed in smaller amounts than the higher solubility acid candidates. Generally, an acid used in the present invention can be present in the receptor medium in an amount ranging from about 1 to about 20 weight percent of the total coating weight of compositions with which the medium is impregnated with a fluid management system/pigment management system according to the disclosure of copending, coassigned, U.S. patent application Ser. No. 08/892,902 (Waller et al.), now U.S. Pat. No. 6,632,510, the disclosure of which is incorporated by reference herein. Preferably, the amount ranges from about 4 to about 15 weight percent. Thus, a sodium salt of an aromatic sulfocarboxylic acid should be present in an amount in the higher end of the range (e.g., about 15 weight percent), whereas a carboxylic acid should be present in an amount in the lower end of the range (e.g., about 5 weight percent).

Moreover, free acid and salt forms of that acid can be combined for controlled tailoring of impregnation processing and resulting drying performance.

The acid or its salt can be impregnated into the media by adding it to a coating solution otherwise being impregnated into the media for fluid management and pigment management purposes. Suitable coating solutions and impregnation techniques are disclosed in copending, coassigned, U.S. patent application Ser. No. 08/892,902, now U.S. Pat. No. 6,632,510, the disclosure of which is incorporated by reference herein for coating on the inkjet receptor medium. Typically, the coating solution comprises a multivalent inorganic salt, a suitable surfactant, an alcohol and water. The weight percent of the acid/salt being used usually ranges from about 40 to about 60 weight percent and more preferably from about 45 to about 55 weight percent of the total solids in the composition.

Pigment Migration Inhibitors

Pigment migration inhibitors can be used in the present invention as an optional additive. These inhibitors can be homopolymers or copolymers having any number of hydrophilic monomers, each of whose homopolymers are hydrophilic, so long as the resulting copolymer is sparingly soluble in water. Pigment migration inhibitors are further disclosed in copending, coassigned, U.S. patent application Ser. No. 09/099,956, now U.S. Pat. No. 6,537,650, the disclosure of which is incorporated herein by reference.

Nonlimiting examples of hydrophilic monomers are methacrylic, ethacrylic acids, acrylic acid, N-Vinylphthalimide, Vinylimidazole, Vinylpyridine and N-vinyl-2-pyrrolidinone, with the last and acrylic acid being presently preferred. The homopolymer is a polyvinylpyrrolidinone (PVP) of relatively high molecular weight available from commercial sources.

Other ink receptive copolymers that are sparingly soluble in water include a copolymer of N-vinylpyrrolidone, acrylic acid, and trimethoxysilylethylmethacrylate (80/10/10); a copolymer of N-vinylpyrrolidone, acrylic acid, trimethoxysilylethylmethacrylate, and ethyleneoxide acrylate (75/10/5/10); a copolymer of N-vinylpyrrolidone, acrylic acid, and N, N, N-methyloctylheptadecafluorosulfonylethylacrylate (MeFOSEA) (80/10/10); a copolymer of N-vinylpyrrolidone, acrylic acid, trimethoxysilylethylmethacrylate and N, N, N-ethyloctylheptadecafluorosulfonylethylacrylate (MeFOSEA) (83/10/2/5); and, a copolymer of N-vinylpyrrolidone, acrylic acid, and Sulfonated Styrene—Sodium Salt (60/10/30).

USEFULNESS OF THE INVENTION AND EXAMPLES

It has been found that ink migration of the pigment particles can occur when capillary forces cause pigment particles of a portion of a printed inkjet medium is partially submerged in water. Only the area of printed ink above migrates, and typically only after several hours of submersion of the other portion of the printed ink. This noticeable ink migration is in a manner like thin layer chromatography.

It has also been found that ink migration of the pigment particles can occur when an overlaminate is used over the printed ink to protect the image. However, at the edge of the overlaminate and the printed ink, water can ingress and cause capillary movement of the pigment underneath the overlaminate.

In the present invention the complexation of multivalent metal cation with the chemically released organic acid anions and the migration inhibitor provides not only efficient pigment and humectant management systems but also allows significant pigment inhibition on the film that it is found to be completely water-fast within 2 minutes to 2 hrs of imaging without mechanical rubbing.

The following examples illustrate the invention in more detail.

Reaction of polyfunctional aromatic compounds containing sulfonic, carboxylic, hydroxyl groups and mixed groups thereof with certain metal halides, pseudo-halides and alkoxides lead to several classes of novel organometallic salts. These salts have been prepared according to the following procedure.

Example 1

Various classes of organometallic salts were prepared by refluxing appropriate quantities of metal chlorides and hydroxysulfonic acids in toluene for 8–9 hrs. The materials were filtered, dried in air and stored. In a typical experiment, to a solution of 90 g of 5-sulfosalicylic acid (0.35 mole) in 100 g toluene was added 15.7 g (0.12 mole) of aluminum chloride and the mixture was heated to near-reflux temperature of the solvent for about 8 hrs. The white solid precipitated was filtered and dried. The product was characterized by the usual analytical techniques.

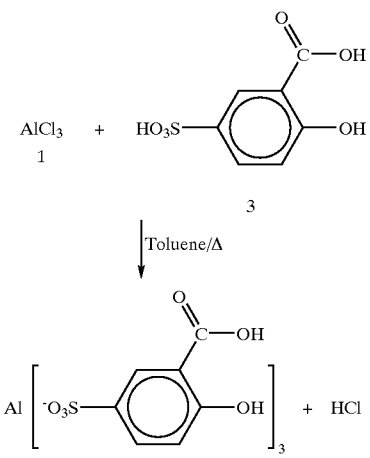

Example 2

The same classes of materials were also prepared by using appropriate metal alkoxides and hydroxysulfonic or sulfocarboxylic acids in water. Thus, aluminum isopropoxide was mixed with 5-sulfophthalic acid in 2:3 molar ratio and the mixture was heated to about 60° C. for about ½ hr. Aluminum isopropoxide was hydrolyzed and the salt was obtained as aqueous solution and was used as such for inkjet coatings. Magnesium ethoxide was similarly hydrolyzed from its mixture with the same acid in 1:2 molar ratio to obtain magnesium sulfophthalate in aqueous solution.

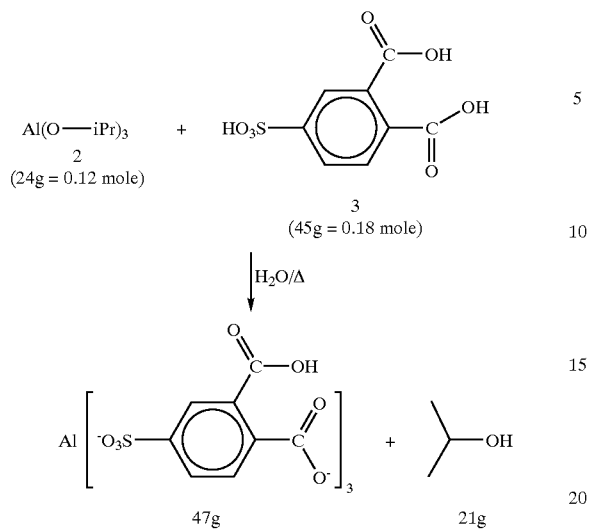

Example 3

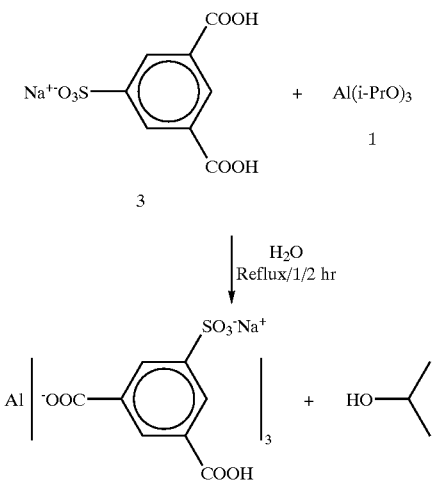

Example 5

The same class of salts were also prepared by yet another procedure Viz. metathetical ion-exchange. Thus, a solution of 5-sulfoisophthalic acid-Na salt (20 g, 0.075 mole) in methanol was mixed with magnesium chloride (3.5 g, 0.0375 mole), and the mixture was refluxed for about ½ hr. The solution was concentrated and sodium chloride was crystallized out. The solution was decanted to obtain 5-sulfoisophthalic acid-Mg salt in solution.

The following organometallic salts (I–IV) were used in the following compositions. The compositions were coated onto oil-in microporous polypropylene membrane prepared by the techniques according to the disclosures of U.S. Pat. Nos. 4,539,256 (Shipman et al.), 4,726,989 (Mrozinski), and more particularly 5,120,594 (Mrozinski). The impregnated membrane was dried and then imaged in an HP-2500 series wide-format inkjet printers (Hewlett Packard Corporation of Palo Alto, Calif., USA) to obtain instantaneously dry, smudge-free and water-fast images.

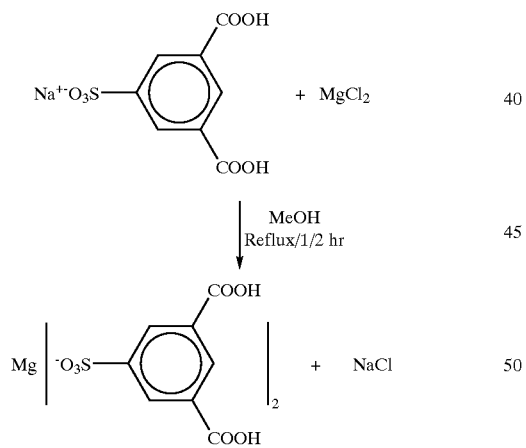

Example 4

Carboxy-derivative of the class of materials were prepared by hydrolyzing metal alkoxide with aromatic carboxylic acid or functionalized aromatic carboxylic acids. Thus, refluxing a mixture of 24 g (0.090 mole) 5-sulfoisophthalic acid-Na salt with 6.1 g (0.030 mole) aluminum isopropoxide in 3:1 molar ratio in aqueous media for about ½ hr, aluminum tris(5-sulfoisophthalate-Na salt) was obtained in solution.

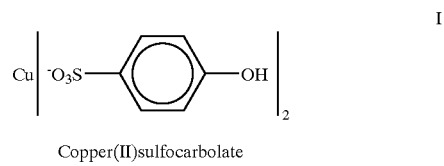

Copper(II)sulfocarbolate

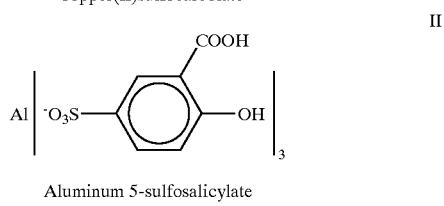

Aluminum 5-sulfosalicylate

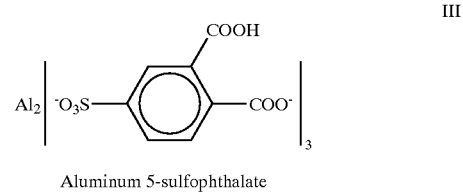

Aluminum 5-sulfophthalate

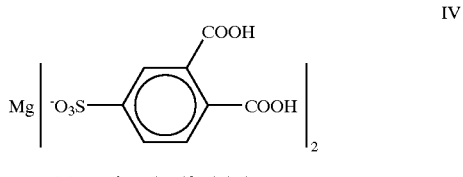

Magnesium 5-sulfophthalate

Composition-I:

|   |   |
|---|---|
| Aluminum 4-sulfophthalate - III | 7.0% |
| Dioctylsulfosuccinate (Dos³) | 5.0% |
| NVP/AA (copolymer) | 2% |
| IPA | 25% |
| De-ionized water | 61% |

Composition-II:

|   |   |
|---|---|
| Copper(II)sulfocarbolate - I | 5.2% |
| Aluminum sulfate (octadecahydrate) | 4.1% |
| Dioctylsulfosuccinate (Dos³) | 7.0% |
| NVP/AA (copolymer) | 2.0% |
| IPA | 25% |
| De-ionized water | 45% |

Composition-III:

|   |   |
|---|---|
| Aluminum 5-sulfosalicylate - II | 7.0% |
| Dioctylsulfosuccinate (Dos³) | 6.0% |
| NVP/AA (copolymer) | 2% |
| IPA | 25% |
| De-ionized water | 60% |

Composition-IV:

|   |   |
|---|---|
| Magnesium 5-sulfophthalate - IV | 5.3% |
| Dioctylsulfosuccinate (Dos³) | 6.0% |
| NVP/AA (copolymer) | 2% |
| IPA | 25% |
| De-ionized water | 60% |

The described compositions were coated onto a microporous polypropylene membrane prepared according to the disclosures of U.S. Pat. Nos. 4,539,256 (Shipman et al.), 4,726,989 (Mrozinski), and more particularly 5,120,594 (Mrozinski) that had the following properties:

|   |   |
|---|---|
| Bubble point | 0.9 µm |
| Gurley 50 cm³ | 15 sec |
| Porosity % void | 38% |
| Surface wetting Energy (before treatment) | 30 dynes/cm² |
| Caliper | 0.178 mm (7 mil) |

The composition was coated onto the microporous inkjet receptor medium with a No. 4 Meyer bar. The printed medium was laminated with 3M Scotch No. 845 Book Tape and the laminated medium was adhered to a piece of anodized aluminum and approximately 75% percent was submerged in water for a period of about 96 hours. During this time of submersion, the image did not show any deterioration due to pigment migration.

The above described examples were repeated successfully using yet another microporous membrane prepared using thermally induced phase separation techniques according to the disclosures of U.S. Pat. Nos. 4,539,256 (Shipman et al.), 4,726,989 (Mrozinski), and more particularly 5,120,594 (Mrozinski), the disclosures of which are incorporated herein by reference. This membrane had the following properties:

|   |   |
|---|---|
| Bubble point | 0.75 µm |
| Gurley 50 cm³ | 20 sec |
| Porosity % void | 41% |
| Surface wetting Energy (before treatment) | 30 dynes/cm² |
| Caliper | 0.178 mm (7 mil) |

The film was dried at about 76° C.–121° C. within 1–2 minutes. The impregnated membrane when imaged in HP-2500 series printer provided very high quality and high-density image which was instantaneously dry, tack-free, feathering-free, and smudge-free. The image did not show any movement in any of the ink/color on water-challenging done in the same manner as disclosed above in the prior example.

The invention is not limited to the above embodiments. The claims follow.

What is claimed is:

1. An inkjet receptor medium suitable for imaging with a pigmented ink, comprising: a porous membrane of a synthetic polymer comprising an anionic surfactant impregnated into pores of the porous membrane; and an organometallic salt of a multivalent metal cation and a multifunctional organic acid anion impregnated into pores of the porous membrane; wherein the organometallic salt is capable of ionizing to a multivalent metal cation and a multifunctional organic acid anion when in contact with an aqueous-based pigmented ink, and further wherein the size of the pores of the porous membrane is at least 0.2 µm, and is no greater than about 2.0 µm, and wherein the pore size is a bubble point pore size measured according to ASTM F-316.

2. The medium of claim 1 wherein the multivalent metal cation is derived from group IIA to VIA or group IB to VIIIB in the Periodic Table.

3. The medium of claim 1, wherein the organic acid anion is selected from the group consisting of acids having a carboxylic, sulfonic, phenolic and mixed functionalities thereof and wherein the organic acid anion is an aromatic acid.

4. The medium of claim 3, wherein the aromatic acid comprises a sulfocarboxylic acid, a sulfosalicylic acid, or a sulfophenolic acid.

5. The medium of claim 1 wherein the organometallic salt is derived from the reaction of a metal halide or a pseudo-halide with an organic acid.

6. The medium of claim 1 wherein the organometallic salt is derived from the reaction of a metal alkoxide with an organic acid via simple hydrolysis in an aqueous medium.

7. The medium of claim 1 wherein the organometallic salt comprises a monomeric, dimeric, or trimeric salt.

8. The medium of claim 1, wherein the porous substrate is a microporous polypropylene membrane.

9. The medium of claim 1, wherein the organometallic salt is a metal sulfocarbolate of the formula:

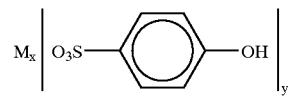

M = Cu, Mg, Co, (x:y = 1:2); M = Al, Ga (x:y = 1:3, 2:3).

10. The medium of claim 1, wherein the organometallic salt is a metal hydroquinonesolfonate of the formula:

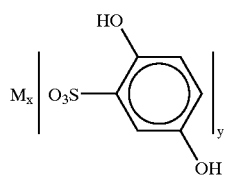

M = Cu, Mg, Co, (x:y = 1:2, 2:2); M = Al, Ga,Ti, Zr (x:y = 1:3, 2:3, 2 :2).

11. The medium of claim 1, wherein the organometallic salt is a metal dihydroxybenzenedisulfonate of the formula:

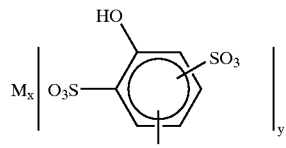

M = Cu, Mg, Co (x:y = 1:1, 1:2); M = Al, Ga, Ti, Zr (x:y = 1:1, 2:2, 4:3).

12. The medium of claim 1, wherein the organometallic salt is a metal sulfosalicylate of the formula:

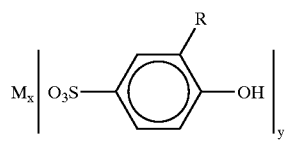

M = Cu, Mg, Co (x:y = 1:2, 1;1); M = Al, Ga, Ti, Zr (x:y = 1:3, 2:3, 3:3)
R = COOH (or a lithium, sodium, or potassium salt thereof).

13. The medium of claim 1, wherein the organometallic salt is a metal sulfophthalate of the formula:

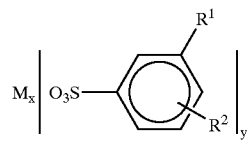

M = Cu, Mg, Co (x:y = 1:1, 2:2, 3:2); M = Al, Ga, Ti, Zr (x:y = 1:3, 2:2, 2:3)
$R^1 = R^2$ = COOH (or a lithium, sodium, or potassium salt thereof).

14. The medium of claim 1, wherein the organometallic salt is a metal carboxylate of the formulae:

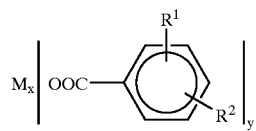

M = Cu, Mg, Co (x:y = 1:1, 2:2, 3:2); M = Al, Ga, Ti, Zr (x:y = 1:3, 2:2, 2:3)
$R^1$ = COOH (or a lithium, sodium, or potassium salt thereof), $R^2$ = OH -continued

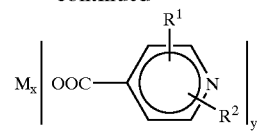

M = Cu, Mg, Co (x:y + 1:1, 2:2, 3:2); M = Al, Ga, Ti, Zr (x:y = 1:3, 2:2, 2:3)
$R^1$ = COOH (or a lithium, sodium, or potassium salt thereof), $R^2$ = OH.

15. The medium of claim 1, wherein the organometallic salt is a metal Calix(4)arene sulfonate of the formula:

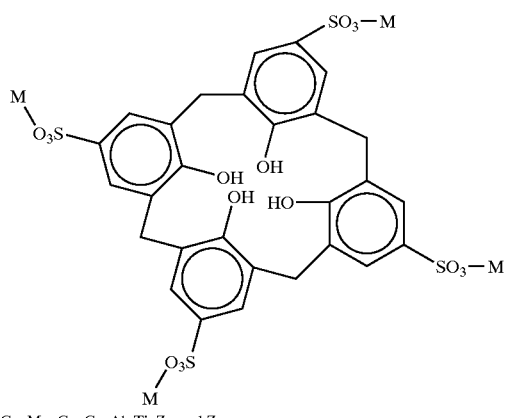

M = Cu, Mg, Co, Ca, Al, Ti, Zr, and Zn.

16. The inkjet receptor medium of claim 1 wherein the porous membrane of a synthetic polymer is a microporous membrane with tortuous paths.

17. The inkjet receptor medium of claim 16 wherein the porous membrane of a synthetic polymer is a thermally induced phase separated microporous membrane.

18. The inkjet receptor medium of claim 1 further comprising an image formed from a pigmented ink.

19. A method of forming an image, the method comprising:

providing an inkjet receptor medium of claim 1; and delivering a pigmented ink to the inkjet receptor medium.

20. The method of claim 19, wherein the receptor medium also includes a migration inhibitor.

21. An inkjet receptor medium suitable for imaging with a pigmented ink comprising; a porous membrane of a synthetic polymer; and an organometallic salt of a multivalent metal cation and a multifunctional organic anion impregnated into pores of the porous membrane; wherein the organometallic salt is capable of ionizing to a multivalent metal cation and a multifunctional organic acid anion when in contact with an aqueous-based pigmented ink, and further wherein the size of the pores of the porous membrane is at least 0.2 μm, and is no greater than about 2.0 μm, and wherein the pore size is a bubble point pore size measured according to ASTM F-316.

* * * * *

UNITED STATES PATENT AND TRADEMARK OFFICE
CERTIFICATE OF CORRECTION

PATENT NO.   : 6,703,112 B1
DATED        : March 9, 2004
INVENTOR(S)  : Farooq, Omar It is certified that error appears in the above-identified patent and that said Letters Patent is hereby corrected as shown below:

Column 6,
Line 28, delete "ect" and insert in place thereof -- etc. --.

Column 9,
Line 20, after "multivalent" delete "10".

Column 14,
Line 57, delete "substrate" and insert in place thereof -- membrane --.
Line 66, after "Co" delete ",".

Column 15,
Line 11, after "Co" delete ",".

Signed and Sealed this

Ninth Day of November, 2004

JON W. DUDAS
*Director of the United States Patent and Trademark Office*

UNITED STATES PATENT AND TRADEMARK OFFICE
CERTIFICATE OF CORRECTION

PATENT NO.    : 6,703,112 B1
DATED         : March 9, 2004
INVENTOR(S)   : Farooq, Omar It is certified that error appears in the above-identified patent and that said Letters Patent is hereby corrected as shown below:

Column 15,
Line 35, delete "1;1" and insert in place thereof -- 1:1 --.

Signed and Sealed this

Twenty-second Day of February, 2005

JON W. DUDAS
*Director of the United States Patent and Trademark Office*